United States Patent
Tang et al.

(10) Patent No.: US 10,801,941 B2
(45) Date of Patent: Oct. 13, 2020

(54) ISOTOPE NUCLEAR MAGNETIC METHOD FOR ANALYZING INEFFECTIVE WATER ABSORPTION OF ROCK PORES

(71) Applicant: China University of Petroleum (East China), Qingdao, Shandong (CN)

(72) Inventors: Mingming Tang, Shandong (CN); Shuangfang Lu, Shandong (CN); Huifang Ma, Shandong (CN); Yang Gao, Shandong (CN); Shunwei Wu, Shandong (CN); Jing Zhang, Shandong (CN); Haisheng Hu, Shandong (CN); Wenbiao Huang, Shandong (CN); Jiafan Tang, Shandong (CN); Min Wang, Shandong (CN); Jijun Li, Shandong (CN); Xueping Liu, Shandong (CN); Hongkun Tan, Shandong (CN); Changhong Chu, Shandong (CN)

(73) Assignee: China University of Petroleum (East China), Qingdao, Shandong (CN)

( * ) Notice: Subject to any disclaimer, the term of this patent is extended or adjusted under 35 U.S.C. 154(b) by 0 days.

(21) Appl. No.: 16/398,033

(22) Filed: Apr. 29, 2019

(65) Prior Publication Data
US 2019/0257733 A1    Aug. 22, 2019

(30) Foreign Application Priority Data
Jun. 9, 2018 (CN) .......................... 2018 1 0590383

(51) Int. Cl.
| G01V 3/00 | (2006.01) |
| G01N 15/08 | (2006.01) |
| G01N 33/24 | (2006.01) |
| G01N 13/00 | (2006.01) |

(52) U.S. Cl.
CPC ......... *G01N 15/0806* (2013.01); *G01N 13/00* (2013.01); *G01N 15/08* (2013.01); *G01N 33/24* (2013.01); *G01N 33/246* (2013.01); *G01N 2015/0813* (2013.01); *G01N 2015/0866* (2013.01)

(58) Field of Classification Search
CPC .............. G01R 33/543; G01R 33/5659; G01R 33/3415; G01R 33/36; A61B 5/055
USPC ........................................................ 324/309
See application file for complete search history.

Primary Examiner — Walter L Lindsay, Jr.
(74) Attorney, Agent, or Firm — Lei Yu

(57) ABSTRACT

An isotope nuclear magnetic method for analyzing ineffective water absorption of rock pores includes steps of: saturating core pores of a core sample with a wetting phase fluid of water $H_2O$, and obtaining a core $T_2$ spectrum after being saturated with the water; re-saturating the core pores with a wetting phase fluid of heavy water $D_2O$, and obtaining a rock baseline $T_2$ spectrum; injecting fluorinated oil into the core sample saturated with the heavy water; injecting the water $H_2O$, simulating a water injection process, and injecting the fluorinated oil, so as to analyze a content of immobile water and obtain a residual $T_2$ spectrum, wherein a range formed by a difference between the residual $T_2$ spectrum and the rock baseline $T_2$ spectrum is an ineffective water absorption portion of the rock pores, and an ineffective water absorption amount is obtained.

2 Claims, 3 Drawing Sheets

ISOTOPE NUCLEAR MAGNETIC METHOD FOR ANALYZING INEFFECTIVE WATER ABSORPTION OF ROCK PORES

CROSS REFERENCE OF RELATED APPLICATION

The present invention claims priority under 35 U.S.C. 119(a-d) to CN 201810590383.0, filed Jun. 9, 2018.

BACKGROUND OF THE PRESENT INVENTION

Field of Invention

The present invention relates to a technical field of development based on water injection, and more particularly to an isotope nuclear magnetic method for analyzing ineffective water absorption of rock pores.

Description of Related Arts

In the process of oilfield development based on water injection, after the injected water enters the reservoir, a part of the water enters the microscopic pores and becomes immobile water. This part of the water is ineffective water absorption of pores.

In the process of oil and gas development, with the continuous extraction of oil and gas, the formation pressure gradually decreases, and the flow rate of oil and gas gradually decreases. In order to supplement the formation energy, it is conventional to use a water injection method. In the practical application of water injection development, it is necessary to quantitatively analyze the ineffective water absorption of the reservoir pores, that is, how much injected water becomes the immobile water. Ineffective water absorption is an important parameter for the design of reservoir water injection development.

There is no exist mature solution for the quantitative analysis of ineffective water absorption of pores.

Conventionally, the scheme for analyzing the water saturation distribution of the reservoir includes an electric resistance method. Because the water saturation is different, the resistance of the rock layer is different. According to the relationship between the electric resistance and the water saturation, the water saturation of the reservoir can be inversely calculated according to the electric resistance. Disadvantages of the resistance method are that the water saturation can be determined, but saturation of the bound water, namely the immobile water, cannot be determined and cannot be used to analyze the ineffective water absorption.

It is also possible to form a two-dimensional porous medium by laser etching or chemical etching on the glass. The dyed water is then used for displacement analysis while video capture is performed. Thereafter, image analysis is used to determine the distribution of the dyed water. Disadvantage of this artificial core method are that only a two-dimensional porous structure can be realized, which is different from the actual three-dimensional core; at the same time, fluid in the micron-sized pores cannot be observed in the video image.

SUMMARY OF THE PRESENT INVENTION

In order to solve the above technical problems, the present invention provides an isotope nuclear magnetic method for analyzing ineffective water absorption of rock pores, which can quantitatively obtain an ineffective amount of immobile water after displacement water is injected into the rock, so as to solve a problem that conventional methods cannot analyze a specific content of ineffective water absorption.

Accordingly, in order to accomplish the above objects, the present invention provides:

an isotope nuclear magnetic method for analyzing ineffective water absorption of rock pores, comprising steps of: saturating core pores of a core sample with a wetting phase fluid of water $H_2O$, and obtaining a core $T_2$ spectrum after being saturated with the water, so as to obtain a conversion relationship between a water volume and a $T_2$ spectrum area; re-saturating the core pores with a wetting phase fluid of heavy water $D_2O$, and obtaining a rock baseline $T_1$ spectrum; injecting fluorinated oil into the core sample saturated with the heavy water to restore original water saturation and oil saturation states of a formation; injecting the water $H_2O$, simulating a water injection process, and injecting the fluorinated oil, so as to analyze a content of immobile water and obtain a residual $T_2$ spectrum, wherein a range formed by a difference between the residual $T_2$ spectrum and the rock baseline $T_2$ spectrum is an ineffective water absorption portion of the rock pores; according to a conversion coefficient of the water volume and the $T_2$ spectrum area, an ineffective water absorption amount is obtained.

The isotope nuclear magnetic method comprises specific steps of:

(1) cleaning and preparing a rock sample;

wherein a cylindrical core sample is obtained by drilling with a diameter of D cm, a length of L cm, and a volume of V; two end faces of the core sample are mechanically polished; oil of the core sample is washed out with an organic solvent, and then the core is dried to complete preparation of the core sample; according to a helium method, a porosity of the core sample is ∅, and a pore volume is VP=V*∅;

(2) saturating with the water $H_2O$;

wherein the cleaned core sample is placed in the water $H_2O$ and stands for no less than 24 hours, so that the core pores are saturated with the wetting phase fluid of the water $H_2O$;

(3) calibrating a ratio relationship of a fluid volume and the $T_2$ spectrum area;

wherein the core sample saturated with the water H2O in the step (2) is placed in a core holder in a magnetic cylinder of a nuclear magnetic displacement instrument, and an external magnetic field B0 of a nuclear magnetic resonance instrument is adjusted to 0.6 T; a frequency of an alternating magnetic field B1 is adjusted to a resonance frequency of protium, and then the core $T_2$ spectrum after being saturated with the water is obtained, wherein an area thereof is TS; according to the area TS and the pore volume VP, a conversion coefficient between a nuclear magnetic signal area and the water volume is determined as $T_2W=VP/TS$;

(4) saturating with the heavy water $D_2O$;

wherein the core sample is washed again according to the step (1); then the cleaned core sample is placed in the heavy water $D_2O$ and stands for no less than 24 hours, so that the core pores are saturated with the wetting phase fluid of the heavy water $D_2O$;

(5) calibrating the rock baseline $T_2$ spectrum;

wherein the core sample saturated with the heavy water D2O in the step (2) is placed in the core holder in the magnetic cylinder of the nuclear magnetic displacement instrument, and the external magnetic field B0 of the nuclear magnetic resonance instrument is adjusted to 0.6 T; the frequency of the alternating magnetic field B1 is adjusted to the resonance frequency of the protium, and then the rock baseline $T_2$ spectrum is obtained; since no $T_2$ signal appears at resonance frequencies of deuterium and protium, the rock baseline $T_2$ spectrum received mainly comes from signals emitted by protium of a rock solid part;

(6) injecting the fluorinated oil;

wherein the fluorinated oil is injected into the core sample saturated with the heavy water by a pressure difference Pcd of oil reservoir filling, and a meter is placed at an outlet to measure a volume VD of the heavy water driven out by the fluorinated oil; when the volume VD is constant, injecting of the fluorinated oil is stopped, and the original water saturation and oil saturation states of the formation are restored;

(7) injecting $H_2O$, and simulating a water flooding process;

wherein after the step (6), the water $H_2O$ is injected into the core sample at a constant speed VI; the water injection process is simulated, and a meter is placed at an outlet to measure a volume VO of the fluorinated oil driven out by the water $H_2O$; when a water injection volume is NPV, injecting of the water $H_2O$ is stopped; NPV=injected liquid volume/total rock pore volume;

(8) injecting the fluorinated oil to analyze the content of the immobile water;

wherein after the step (7), the fluorinated oil is injected into the core sample at the constant speed VI, and a meter is placed at the outlet to measure a volume VH of the water $H_2O$ driven out by the fluorinated oil; when the volume VH is constant, injecting of the fluorinated oil is stopped, and remaining water in the core is the immobile water; and (9) determining the ineffective water absorption of the core pores;

wherein the remaining water in the core sample of the step (8) is the immobile water; after the step (8), the external magnetic field B0 of the nuclear magnetic resonance instrument is adjusted to 0.6 T, and the frequency of the alternating magnetic field B1 is adjusted to the resonance frequency of the protium; since the heavy water has no nuclear magnetic echo signal under the resonance frequency of the protium, a $T_2$ spectrum signal after injecting the fluorinated oil into the core in the step (8) is a residual water signal, which is called the residual $T_2$ spectrum; an ineffective water absorption $T_2$ spectrum after core injection is obtained according to the difference between the residual $T_2$ spectrum and the rock baseline $T_2$ spectrum in the step (5), and the range formed by the difference is the ineffective water absorption portion of the rock pores, wherein an spectrum area of the ineffective water absorption portion is WTS; according to the conversion coefficient $T_2W$ calibrated in the step (3) by the ratio relationship of the fluid volume and the $T_2$ spectrum area, a specific volume the immobile water converted from the water injected into the core is $Vfa=WTS*T_2W$; according to a conversion relationship between a $T_2$ spectrum relaxation time and a pore radius, pore size distribution of the rock pores with ineffective water absorption is obtained from the ineffective water absorption $T_2$ spectrum after core injection.

The isotope nuclear magnetic method for analyzing the ineffective water absorption of the rock pores provided by the present invention combines displacement, isotope labeling and nuclear magnetic $T_2$ spectrum analysis by using different nuclear magnetic response signals of water and heavy water, so as to determine the source of the immobile water in the rock and the ineffective water injection amount. The sample baseline $T_2$ spectrum is first determined, and the difference between the residual $T_2$ spectrum and the baseline $T_2$ spectrum is taken as a $T_2$ spectrum part of final ineffective water absorption, which effectively reduces the influence of the protium element in the sample.

DETAILED DESCRIPTION OF THE PREFERRED EMBODIMENT

According to an embodiment, the present invention will be further illustrated.

Analyze of inefficient water absorption of sandstone in the Fuyu oil layer in Daqing is provided, wherein a core sample is processed to be 2.5 cm in diameter and 6 cm in axis length.

Figure 2:
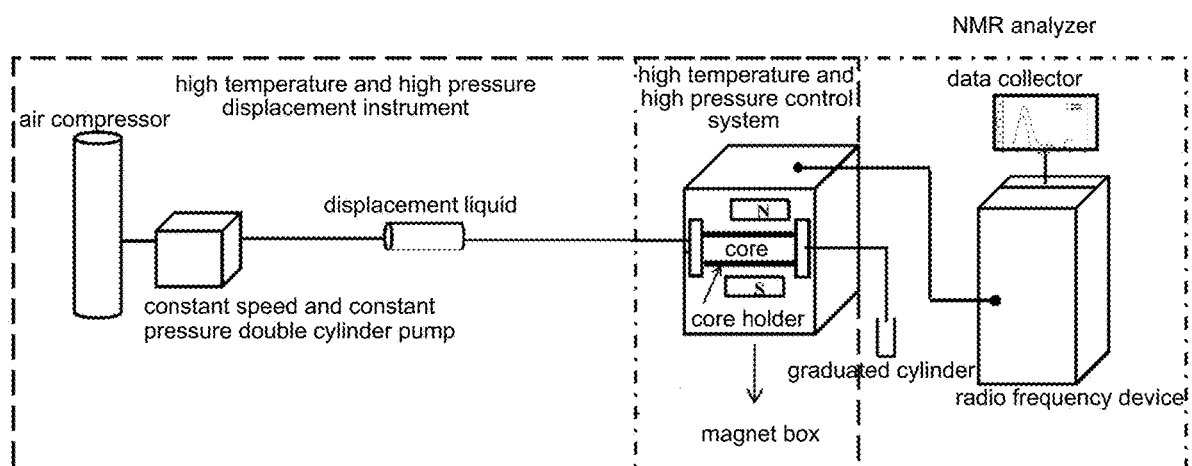
FIG. 2 is a sketch view of a nuclear magnetic displacement instrument system.

FIG. 2 shows a nuclear magnetic displacement instrument according to the embodiment; which comprises an air compressor, a constant speed and constant pressure double cylinder pump, a displacement liquid tank, a fluorinated oil tank, a magnet box, and a radio frequency device. The magnet box provides a stable external field B0, and the radio frequency device comprises an alternating signal B1 and a nuclear magnetic resonance echo signal detecting probe.

The instrument uses the following steps of:

(1) placing the core sample in a core holder in a sample cylinder of the magnet box;

(2) adjusting a high temperature and high pressure control system of the magnet box, in such a manner that a temperature and a pressure of the core holder reaches formation temperature and pressure conditions;

(3) pressing liquid into the core according to a constant temperature or constant pressure method; and (4) turning on the radio frequency device to collect the $T_2$ spectrum signal of the core sample.

The isotope nuclear magnetic method for analyzing the ineffective water absorption of the rock pores of the present invention utilizes two hydrogen isotopes protium H and deuterium D, and different nuclear magnetic signal responses of two isotopic water molecules $H_2O$ and $D_2O$ under the same external magnetic field strength and excitation frequency. Therefore, quantitative analysis of an ineffective water absorption amount of the rock pores is realized by combining the displacement method.

Among them, the principle of nuclear magnetic resonance is: the nucleus is a positively charged particle, the non-spinning nucleus has no magnetic moment, and the spinable nucleus has a circulating current, which generates a magnetic field and forms a magnetic moment ($\mu$). When the spinning nucleus is in an external magnetic field with an intensity of B0 in addition to spin, the nucleus also moves around the B0. Such movement is similar to the movement of gyro, called Larmor precession. Angular velocity $\omega 0$ of spinning nucleus precession is proportional to the intensity B0 of the external magnetic field, and a proportionality constant is a magnetogyric ratio $\gamma$: $\omega 0=2\pi v0=\gamma B0$, wherein v0 is a precession frequency.

Orientation of microscopic magnetic moments under an external magnetic field is quantized, and nuclei with a spin quantum number I may have only 2I+1 orientations under the external magnetic field, wherein each orientation can be represented by a spin magnetic quantum number m, and a relationship between m and I is:

m=I, I−1, I−2 . . . −I

Each orientation of the nucleus represents an energy state of the nucleus in the magnetic field.

Let the spin nuclei in the external magnetic field B0 be excited by an alternating magnetic field B1 perpendicular to B0. When radiation energy from the B1 is exactly equal to the energy difference between two different orientations of the spin nuclei, the spin nuclei in the low energy state E1 absorbs electromagnetic radiation energy and transitions to the high energy state E2. This phenomenon is called nuclear magnetic resonance, referred to as NMR.

$T_1$ relaxation time and $T_2$ relaxation time are that: when the excitation alternating magnetic field B1 is removed, the spin nucleus will automatically transition from the high energy state E2 to the low energy state E1 under the action of B0. This process is called relaxation. In this process, the number of nuclei on the low energy state E1 gradually increases. This increasing process is called longitudinal relaxation, and the relaxation time taken by the increase process is $T_1$. At the same time, the nuclear spin direction in the high-energy state E2 also changes laterally, but such energy invariance process is called transverse relaxation. The lateral relaxation causes the excitation magnetic field to be dispersed, and the relaxation time taken by the reduction process is $T_2$. The lateral direction refers to all horizontal directions perpendicular to the magnetic field B0. Longitudinal relaxation is an energy relaxation phenomenon, which is an energy entropy increase process; transverse relaxation is a geometric phase relaxation phenomenon, which is a geometric entropy increasing process.

Porous media is: a media containing complex pore-throat structures, such as sandstone, shale, etc.

Relationship between fluid relaxation time $T_2$ and pore size r in porous media is as follows.

The mechanism for determining the transverse phase relaxation time $T_2$ of a fluid nucleus in a porous medium is as follows:

$$\frac{1}{T_2} = \frac{1}{T_{2B}} + \rho\left(\frac{S}{V}\right) + \frac{D(\gamma GT_E)^2}{12} \quad (1)$$

wherein $$\frac{1}{T_{2B}}$$

is a transverse volume relaxation term, $T_{2B}$ is a free relaxation time of the fluid;

$$\rho\left(\frac{S}{V}\right)$$

is a transverse surface relaxation term, S is a pore surface area, V is a pore volume, ρ is a transverse relaxation strength factor;

$$\frac{D(\gamma GT_E)^2}{12}$$

is a diffusion relaxation term, G is a magnetic field gradient, $T_E$ is an echo interval, γ is a magnetogyric ratio, and D is a diffusion coefficient.

When there is only one kind of fluid in the pores, $T_{2B}$ is much larger than $T_2$, so the lateral volume relaxation term $$\frac{1}{T_{2B}}$$

can be ignored; when the magnetic field is sufficiently uniform, the magnetic field gradient is very small, and the echo interval $T_E$ is small, the diffusion relaxation term $$\frac{D(\gamma GT_E)^2}{12}$$

can also be ignored. Under the above conditions, the transverse relaxation time is only related to the transverse surface relaxation $$\rho\left(\frac{S}{V}\right): \frac{1}{T_2} \approx \rho\left(\frac{S}{V}\right) = \rho\frac{F}{r},$$

wherein F is a shape factor and r is a pore radius. The above shows that for the fluid in the small-diameter pores, the faster the phase is laterally dispersed, the shorter the transverse relaxation time will be, and the magnetization of the fluid in this part of the pores is earliest reduced; for the fluid in the large-diameter pores, the slower the phase is laterally dispersed, the longer the transverse relaxation time will be, and the magnetization of the fluid in this part of the pores is latest reduced.

Figure 1:
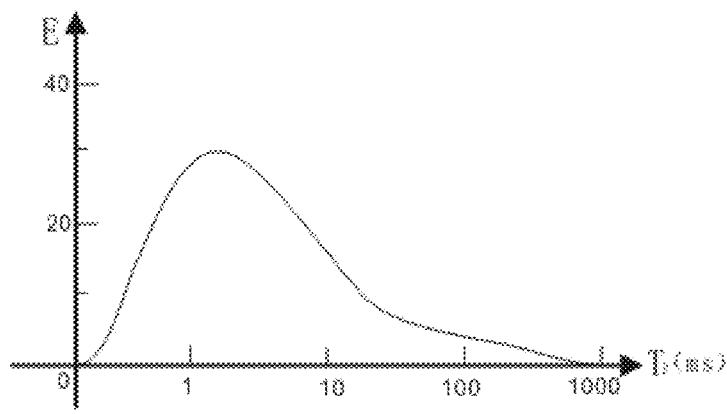
FIG. 1 is a rock nuclear magnetic $T_2$ spectrum.

For the rock nuclear magnetic $T_2$ spectrum: since the pore radius of the porous medium has a division f(r) and the relaxation time $T_2$ of different radius r is different, the transverse relaxation time of the porous medium is not a single value, but a division-$T_2$ division. The spin echo string measured and recorded by nuclear magnetic pulse sequence is exponentially attenuated, which means that single exponential attenuations are superposed:

$$A_j = \sum_i E_i e^{-\frac{j\Delta T_{CE}}{T_{2i}}} \quad (i = 1, \ldots, N; j = 1, \ldots, M) \quad (2)$$

wherein $A_j$ is a measured amplitude of the j-th echo signal, $\Delta T_{CE}$ is a measure echo interval, $T_{2i}$ is a transverse relaxation time constant of the i-th pore fluid, $E_i$ is a transverse relaxation intensity of the i-th pore. Multi-exponential fitting of the echo signals presets multiple T2($T_{2i}$) values, and then find multiple $E_i$, so that it can fit the measured echo signals $T_{2i}$ and $E_i$ form the nuclear magnetic T2 spectrum as shown in FIG. 1, wherein $T_{2i}$ corresponds to an pore radius, $E_i$ corresponds to a volume of the pores with such pore radius. A bottom portion area of the T2 spectrum corresponds to a total fluid volume in the rock pores.

Figure 3:
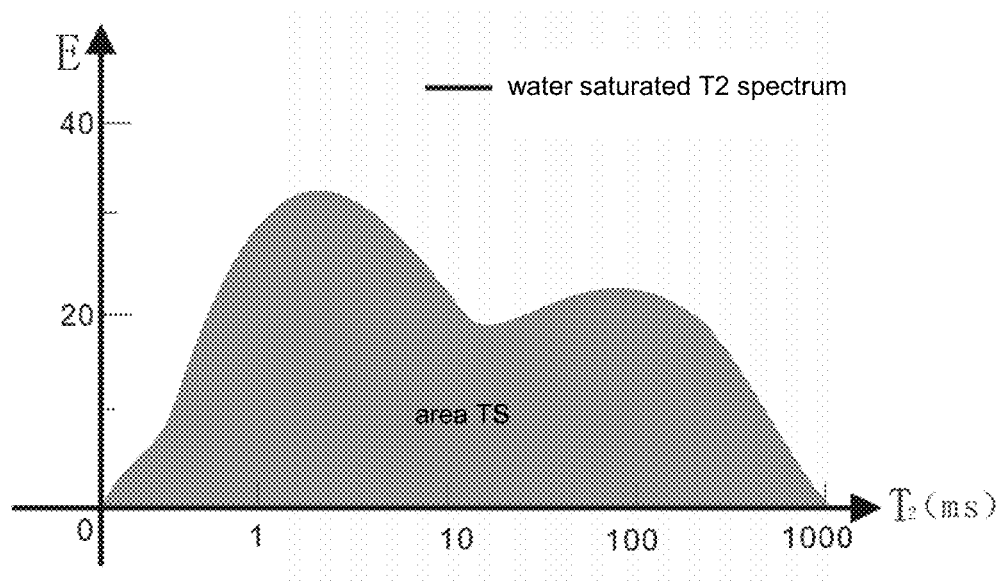
FIG. 3 is a $T_2$ spectrum when core pores are saturated with water according to an embodiment.
Figure 4:
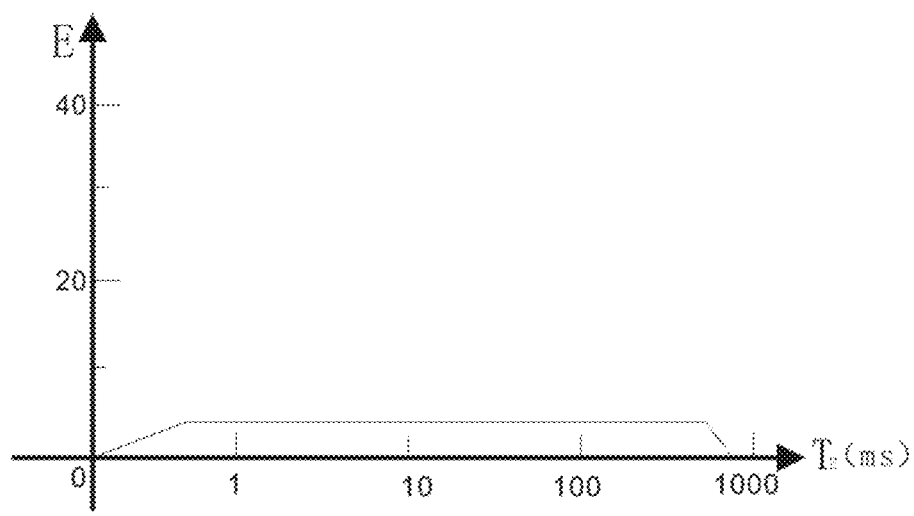
FIG. 4 illustrates a baseline of the rock $T_2$ spectrum according to the embodiment.
Figure 5:
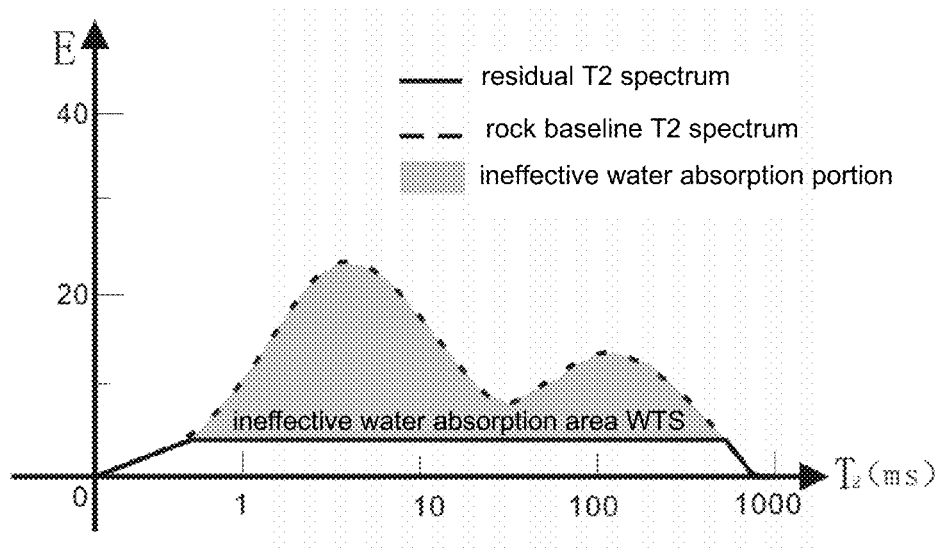
FIG. 5 is an ineffective water absorption $T_2$ spectrum after water injection according to the embodiment.

The isotope nuclear magnetic method comprises specific steps of:

(1) cleaning and preparing a rock sample;

wherein a cylindrical core sample is obtained by drilling with a diameter of D cm, a length of L cm, and a volume of V; two end faces of the core sample are mechanically polished; oil of the core sample is washed out with an organic solvent, and then the core is dried to complete preparation of the core sample; according to a helium method, a porosity of the core sample is $\emptyset$, and a pore volume is $VP=V*\emptyset$;

(2) saturating with the water $H_2O$;

wherein the cleaned core sample is placed in the water $H_2O$ and stands for no less than 24 hours, so that the core pores are saturated with the wetting phase fluid of the water $H_2O$;

(3) calibrating a ratio relationship of a fluid volume and the $T_2$ spectrum area;

wherein the core sample saturated with the water H2O in the step (2) is placed in a core holder in a magnetic cylinder of a nuclear magnetic displacement instrument, as shown in FIG. 2, and an external magnetic field B0 of a nuclear magnetic resonance instrument is adjusted to 0.6 T; a frequency of an alternating magnetic field B1 is adjusted to a resonance frequency of protium, and then the core $T_2$ spectrum after being saturated with the water is obtained, as shown in FIG. 3, wherein an area thereof is TS; according to the area TS and the pore volume VP, a conversion coefficient between a nuclear magnetic signal area and the water volume is determined as $T_2W=VP/TS$;

(4) saturating with the heavy water $D_2O$;

wherein the core sample is washed again according to the step (1); then the cleaned core sample is placed in the heavy water $D_2O$ and stands for no less than 24 hours, so that the core pores are saturated with the wetting phase fluid of the heavy water $D_2O$;

(5) calibrating the rock baseline $T_2$ spectrum;

wherein the core sample saturated with the heavy water D2O in the step (2) is placed in the core holder in the magnetic cylinder of the nuclear magnetic displacement instrument, and the external magnetic field B0 of the nuclear magnetic resonance instrument is adjusted to 0.6 T; the frequency of the alternating magnetic field B1 is adjusted to the resonance frequency of the protium, and then the rock baseline $T_2$ spectrum is obtained, as shown in FIG. 4; since no $T_2$ signal appears at resonance frequencies of deuterium and protium, the rock baseline $T_2$ spectrum received mainly comes from signals emitted by protium of a rock solid part;

(6) injecting the fluorinated oil;

wherein the fluorinated oil is injected into the core sample saturated with the heavy water by a pressure difference Pcd of oil reservoir filling, and a meter is placed at an outlet to measure a volume VD of the heavy water driven out by the fluorinated oil; when the volume VD is constant, injecting of the fluorinated oil is stopped, and the original water saturation and oil saturation states of the formation are restored;

(7) injecting the water $H_2O$, and simulating a water flooding process;

wherein after the step (6), the water $H_2O$ is injected into the core sample at a constant speed VI; the water injection process is simulated, and a meter is placed at an outlet to measure a volume VO of the fluorinated oil driven out by the water $H_2O$; when a water injection volume is NPV, injecting of the water $H_2O$ is stopped; NPV=injected liquid volume/ total rock pore volume;

(8) injecting the fluorinated oil to analyze the content of the immobile water;

wherein after the step (7), the fluorinated oil is injected into the core sample at the constant speed VI, and a meter is placed at the outlet to measure a volume VH of the water $H_2O$ driven out by the fluorinated oil; when the volume VH is constant, injecting of the fluorinated oil is stopped, and remaining water in the core is the immobile water; and (9) determining the ineffective water absorption of the core pores;

wherein the remaining water in the core sample of the step (8) is the immobile water; after the step (8), the external magnetic field B0 of the nuclear magnetic resonance instrument is adjusted to 0.6 T, and the frequency of the alternating magnetic field B1 is adjusted to the resonance frequency of the protium; since the heavy water has no nuclear magnetic echo signal under the resonance frequency of the protium, a $T_2$ spectrum signal after injecting the fluorinated oil into the core in the step (8) is a residual water signal, which is called the residual $T_2$ spectrum; an ineffective water absorption $T_2$ spectrum after core injection is obtained according to the difference between the residual $T_2$ spectrum and the rock baseline $T_2$ spectrum in the step (5), as shown in FIG. 5, and the range formed by the difference is the ineffective water absorption portion of the rock pores, wherein an spectrum area of the ineffective water absorption portion is WTS; according to the conversion coefficient $T_2W$ calibrated in the step (3) by the ratio relationship of the fluid volume and the $T_2$ spectrum area, a specific volume the immobile water converted from the water injected into the core is $Vfa=WTS*T_2W$, according to a conversion relationship between a $T_2$ spectrum relaxation time and a pore radius, pore size distribution of the rock pores with ineffective water absorption is obtained from FIG. 5 the ineffective water absorption $T_2$ spectrum after core injection.

For the sandstone in the Fuyu oil layer in Daqing, the amount of ineffective water absorption converted from water injection is 0.4 ml. However, conventional resistance method and artificial core experimental method cannot obtain the ineffective water absorption.

What is claimed:

1. An isotope nuclear magnetic method for analyzing ineffective water absorption of rock pores, comprising steps of: saturating core pores of a core sample with a wetting phase fluid of water $H_2O$, and obtaining a core $T_2$ spectrum after being saturated with the water, so as to obtain a conversion relationship between a water volume and a $T_2$ spectrum area; re-saturating the core pores with a wetting phase fluid of heavy water $D_2O$, and obtaining a rock baseline $T_2$ spectrum; injecting fluorinated oil into the core sample saturated with the heavy water to restore original water saturation and oil saturation states of a formation; injecting the water $H_2O$, simulating a water injection process, and injecting the fluorinated oil, so as to analyze a content of immobile water and obtain a residual $T_2$ spectrum, wherein a range formed by a difference between the residual $T_2$ spectrum and the rock baseline $T_2$ spectrum is an ineffective water absorption portion of the rock pores; according to a conversion coefficient of the water volume and the $T_2$ spectrum area, an ineffective water absorption amount is obtained.

2. The isotope nuclear magnetic method, as recited in claim 1, comprising specific steps of:

(1) cleaning and preparing a rock sample;

wherein a cylindrical core sample is obtained by drilling with a diameter of D cm, a length of L cm, and a volume of V; two end faces of the core sample are mechanically polished; oil of the core sample is washed out with an organic solvent, and then the core is dried to complete preparation of the core sample; according to a helium method, a porosity of the core sample is $\emptyset$, and a pore volume is $VP=V*\emptyset$;

(2) saturating with the water $H_2O$;
wherein the cleaned core sample is placed in the water $H_2O$ and stands for no less than 24 hours, so that the core pores are saturated with the wetting phase fluid of the water $H_2O$;
(3) calibrating a ratio relationship of a fluid volume and the $T_2$ spectrum area;
wherein the core sample saturated with the water H2O in the step (2) is placed in a core holder in a magnetic cylinder of a nuclear magnetic displacement instrument, and an external magnetic field B0 of a nuclear magnetic resonance instrument is adjusted to 0.6 T; a frequency of an alternating magnetic field B1 is adjusted to a resonance frequency of protium, and then the core $T_2$ spectrum after being saturated with the water is obtained, wherein an area thereof is TS; according to the area TS and the pore volume VP, a conversion coefficient between a nuclear magnetic signal area and the water volume is determined as $T_2W=VP/TS$;
(4) saturating with the heavy water $D_2O$;
wherein the core sample is washed again according to the step (1); then the cleaned core sample is placed in the heavy water $D_2O$ and stands for no less than 24 hours, so that the core pores are saturated with the wetting phase fluid of the heavy water $D_2O$;
(5) calibrating the rock baseline $T_2$ spectrum;
wherein the core sample saturated with the heavy water D2O in the step (2) is placed in the core holder in the magnetic cylinder of the nuclear magnetic displacement instrument, and the external magnetic field B0 of the nuclear magnetic resonance instrument is adjusted to 0.6 T; the frequency of the alternating magnetic field B1 is adjusted to the resonance frequency of the protium, and then the rock baseline $T_2$ spectrum is obtained; since no $T_2$ signal appears at resonance frequencies of deuterium and protium, the rock baseline $T_2$ spectrum received mainly comes from signals emitted by protium of a rock solid part;
(6) injecting the fluorinated oil;
wherein the fluorinated oil is injected into the core sample saturated with the heavy water by a pressure difference Pcd of oil reservoir filling, and a meter is placed at an outlet to measure a volume VD of the heavy water driven out by the fluorinated oil; when the volume VD is constant, injecting of the fluorinated oil is stopped, and the original water saturation and oil saturation states of the formation are restored;
(7) injecting the water $H_2O$, and simulating a water flooding process;
wherein after the step (6), the water $H_2O$ is injected into the core sample at a constant speed VI; the water injection process is simulated, and a meter is placed at an outlet to measure a volume VO of the fluorinated oil driven out by the water $H_2O$; when a water injection volume is NPV, injecting of the water $H_2O$ is stopped; NPV=injected liquid volume/total rock pore volume;
(8) injecting the fluorinated oil to analyze the content of the immobile water;
wherein after the step (7), the fluorinated oil is injected into the core sample at the constant speed VI, and a meter is placed at the outlet to measure a volume VH of the water $H_2O$ driven out by the fluorinated oil; when the volume VH is constant, injecting of the fluorinated oil is stopped, and remaining water in the core is the immobile water; and
(9) determining the ineffective water absorption of the core pores;
wherein the remaining water in the core sample of the step (8) is the immobile water; after the step (8), the external magnetic field B0 of the nuclear magnetic resonance instrument is adjusted to 0.6 T, and the frequency of the alternating magnetic field B1 is adjusted to the resonance frequency of the protium; since the heavy water has no nuclear magnetic echo signal under the resonance frequency of the protium, a $T_2$ spectrum signal after injecting the fluorinated oil into the core in the step (8) is a residual water signal, which is called the residual $T_2$ spectrum; an ineffective water absorption $T_2$ spectrum after core injection is obtained according to the difference between the residual $T_2$ spectrum and the rock baseline $T_2$ spectrum in the step (5), and the range formed by the difference is the ineffective water absorption portion of the rock pores, wherein an spectrum area of the ineffective water absorption portion is WTS; according to the conversion coefficient $T_2W$ calibrated in the step (3) by the ratio relationship of the fluid volume and the $T_2$ spectrum area, a specific volume the immobile water converted from the water injected into the core is $Vfa=WTS*T_2W$; according to a conversion relationship between a $T_2$ spectrum relaxation time and a pore radius, pore size distribution of the rock pores with ineffective water absorption is obtained from the ineffective water absorption $T_2$ spectrum after core injection.

* * * * *